(12) United States Patent
Rane

(10) Patent No.: US 8,585,577 B2
(45) Date of Patent: Nov. 19, 2013

(54) MULTI-LEVELED TRANSGLUTEAL TENSION-FREE LEVATORPLASTY FOR TREATMENT OF RECTOCELE

(75) Inventor: Ajay Rane, Townsville (AU)

(73) Assignee: AMS Research Corporation, Minnetonka, MN (US)

( * ) Notice: Subject to any disclaimer, the term of this patent is extended or adjusted under 35 U.S.C. 154(b) by 910 days.

(21) Appl. No.: 12/087,552

(22) PCT Filed: Jan. 10, 2007

(86) PCT No.: PCT/IB2007/000584
§ 371 (c)(1),
(2), (4) Date: Jul. 9, 2008

(87) PCT Pub. No.: WO2007/080519
PCT Pub. Date: Jul. 19, 2007

(65) Prior Publication Data
US 2009/0005634 A1    Jan. 1, 2009

Related U.S. Application Data

(60) Provisional application No. 60/757,615, filed on Jan. 10, 2006.

(51) Int. Cl.
*A61F 2/00* (2006.01)

(52) U.S. Cl.
USPC .......................................................... 600/37

(58) Field of Classification Search
USPC .................. 600/29–32, 37; 128/885; 606/151
See application file for complete search history.

(56) References Cited

U.S. PATENT DOCUMENTS

| 5,013,292 | A  | * | 5/1991 | Lemay ............................ 600/30 |
| 6,802,807 | B2 |   | 10/2004 | Anderson et al. |
| 6,911,003 | B2 |   | 6/2005 | Anderson et al. |
| 6,971,986 | B2 |   | 12/2005 | Staskin et al. |
| 7,048,682 | B2 |   | 5/2006 | Neisz et al. |
| 2002/0028980 | A1 |   | 3/2002 | Theirfelder et al. |
| 2002/0072694 | A1 |   | 6/2002 | Snitkin et al. |
| 2003/0220538 | A1 | * | 11/2003 | Jacquetin ........................ 600/37 |
| 2005/0245787 | A1 |   | 11/2005 | Cox et al. |
| 2005/0250977 | A1 |   | 11/2005 | Montpetit et al. |
| 2006/0058575 | A1 | * | 3/2006 | Zaddem et al. ................. 600/30 |

FOREIGN PATENT DOCUMENTS

| GB | 2407988 | 5/2006 |
| WO | WO 03/053252 | 7/2003 |
| WO | WO 03/096929 | 11/2003 |
| WO | WO 2004/012626 | 2/2004 |

* cited by examiner

*Primary Examiner* — Christine Matthews
(74) *Attorney, Agent, or Firm* — Kagan Binder, PLLC

(57) ABSTRACT

Improved methods for treatment of pelvic organ prolapse are provided. Mesh implants are placed in the appropriate locations to effect multi-level support. The method is accomplished via a transgluteal approach.

5 Claims, 4 Drawing Sheets

MULTI-LEVELED TRANSGLUTEAL TENSION-FREE LEVATORPLASTY FOR TREATMENT OF RECTOCELE

The present non-provisional patent application claims benefit from International Application No. PCT/IB2007/000584, having PCT Publication No. WO 2007/080519 A2, which was filed on Jan. 10, 2007, which in turn claims priority under 35 USC §119(e) from United States Provisional Patent Application having Ser. No. 60/757,615, filed on Jan. 10, 2006, by Ajay Rane, and titled "Multi-leveled Transgluteal Tension-free Levatorplasty For Treatment of Rectocele," wherein the entirety of said provisional patent application is incorporated herein by reference.

BACKGROUND OF THE INVENTION

1. Field of the Invention

This invention relates to urogenital surgery.

2. Description of the Related Art

Female genital prolapse has long plagued women. It is estimated by the U.S. National Center for Health Statistics that 247,000 operations for genital prolapse were performed in 1998. With the increasing age of the U.S. population, these problems will likely assume additional importance.

The common clinical symptoms of vaginal prolapse are related to the fact that, following hysterectomy, the vagina is inappropriately serving the role of a structural layer between intra-abdominal pressure and atmospheric pressure. This pressure differential puts tension on the supporting structures of the vagina, causing a "dragging feeling" where the tissues connect to the pelvic wall or a sacral backache due to traction on the uterosacral ligaments. Exposure of the moist vaginal walls leads to a feeling of perineal wetness and can lead to ulceration of the exposed vaginal wall. Vaginal prolapse may also result in loss of urethral support due to displacement of the normal structural relationship, resulting in stress urinary incontinence. Certain disruptions of the normal structural relationships can result in urinary retention, as well. Stretching of the bladder base is associated with vaginal prolapse and can result in complaints of increased urinary urgency and frequency. Other symptoms, such as anal incontinence and related bowel symptoms, and sexual dysfunction are also frequently seen with vaginal prolapse.

Anterior vaginal wall prolapse causes the vaginal wall to fail to hold the bladder in place. This condition, in which the bladder sags or drops into the vagina, is termed a cystocele. There are two types of cystocele caused by anterior vaginal wall prolapse. Paravaginal defect is caused by weakness in the lateral supports (pubourethral ligaments and attachment of the bladder to the endopelvic fascia); central defect is caused by weakness in the central supports. There may also be a transverse defect, causing cystocele across the vagina.

Posterior vaginal wall prolapse results in descent of the rectum into the vagina, often termed a rectocele, or the presence of small intestine in a hernia sac between the rectum and vagina, called an enterocele. Broadly, there are four types based on suspected etiology. Congenital enteroceles are thought to occur because of failure of fission or reopening of the fused peritoneal leaves down to the perineal body. Posthysterectomy vault prolapses may be "pulsion" types that are caused by pushing with increased intra-abdominal pressure. They may occur because of failure to reapproximate the superior aspects of the pubocervical fascia and the rectovaginal fascia at the time of surgery. Enteroceles that are associated with cystocele and rectocele may be from "traction" or pulling down of the vaginal vault by the prolapsing organs. Finally, iatrogenic prolapses may occur after a surgical procedure that changes the vaginal axis, such as certain surgical procedures for treatment of incontinence. With regard to rectoceles, low rectoceles may result from disruption of connective tissue supports in the distal posterior vaginal wall, perineal membrane, and perineal body. Mid-vaginal and high rectoceles may result from loss of lateral supports or defects in the rectovaginal septum. High rectoceles may result from loss of apical vaginal supports. Posterior or posthysterectomy enteroceles may accompany rectoceles.

Several factors have been implicated as being involved in genital prolapse in women. It is thought that individual women have differing inherent strength of the relevant connective tissue. Further, loss of connective tissue strength might be associated with damage at childbirth, deterioration with age, poor collagen repair mechanisms, and poor nutrition. Loss of muscle strength might be associated with neuromuscular damage during childbirth, neural damage from chronic straining, and metabolic diseases that affect muscle function. Other factors involved in prolapse include increased loads on the supportive system, as seen in prolonged lifting or chronic coughing from chronic pulmonary disease, or some disturbance in the balance of the structural support of the genital organs. Obesity, constipation, and a history of hysterectomy have also been implicated as possible factors.

As noted, vaginal prolapse and the concomitant anterior cystocele can lead to discomfort, urinary incontinence, and incomplete emptying of the bladder. Posterior vaginal prolapse may additionally cause defecatory problems, such as tenesmus and constipation. Furthermore, apart from the physical symptoms, vaginal prolapse has been shown to result in a lower quality of life for its sufferers, including feeling less attractive, less feminine, and less sexually attractive.

Vaginal prolapse develops when intra-abdominal pressure pushes the vagina outside the body. In a normal situation, the levator ani muscles close the pelvic floor. This results in little force being applied to the fascia and ligaments that support the genital organs. Increases in abdominal pressure, failure of the muscles to keep the pelvic floor closed, and damage to the ligaments and fascia all contribute to the development of prolapse. In addition, if a woman has a hysterectomy, the vaginal angle may be altered, causing increased pressure at a more acute angle, accelerating the prolapse.

There are generally two different types of tissue that make up the supportive structure of the vagina and uterus. First, there are fibrous connective tissues that attach these organs to the pelvic walls (cardinal and uterosacral ligaments; pubocervical and rectovaginal fascia). Second, the levator ani muscles close the pelvic floor so the organs can rest on the muscular shelf thereby provided. It is when damage to the muscles opens the pelvic floor or during the trauma of childbirth that the fascia and ligaments are strained. Breaks in the fascia allow the wall of the vagina or cervix to prolapse downward.

As noted above, the levator ani muscles close the pelvic floor so the organs can rest on the muscular shelf thereby provided. The levator ani muscles arise from the pubis, the pelvic fascia, and the ischial spine. They insert on the pelvic viscera, coccyx, and the fibrous raphe of the perineum.

When damage has occurred in the levator muscle, most commonly as a result of obstetric injury, the anatomical defect is noted as a tendency towards a vertical elongation of the levator plate. This downward sagging of the levator plate results in the longitudinal enlargement of the levator hiatus with secondary placement of the cervix and upper vagina upon the levator hiatus. With increased intra-abdominal pressure the defective levator plate is no longer supportive of the downward movement of the uterus, cervix and upper vagina, which are resting upon the levator hiatus, and genital prolapse develops. Over a period of time elongation of the uterosacral and cardinal ligaments will result.

The cardinal and uterosacral ligaments form a suspensory mechanism that suspends the vaginal apex but allows for some vertical mobility. In the normal woman the cervix will descend to but not below the plane of the ischial spines. Damage to the cardinal uterosacral ligament complex permits the uterus and upper vagina to telescope downwards, like an inverted sock. Complete failure of the cardinal uterosacral ligament complex will result in a "cervix-first" prolapse.

Anteriorly, the continence mechanism is maintained by the integrity of the sub-urethral hammock and the insertion of pubo-urethral ligaments into the mid urethra. Posteriorly, the perineal body needs to be firm and substantial in size to allow stretching and angulation of the vagina around it. Levator muscle distension can have a significant effect on perineal body descent and future pelvic prolape, as well as prolapse recurrence.

Treatment of vaginal prolapse is uncertain, and generally based on the symptoms of the prolapse. If symptoms are more severe, treatment is commonly by either surgery or pessary. Surgical options might include hysterectomy or by uterus-saving procedures. Such procedures may include abdominal or vaginal access routes. Sacralcolpopexy or sacrospinous fixation may be used. Anterior colporrhaphy is often utilized for treatment of anterior vaginal prolapse. In addition, methods of surgical repair using mesh or biological implants, or a combination thereof, to support the prolapsed organ in its appropriate position, have been developed, and may use either a transobturator or vaginal approach.

Traditional anterior prolapse repairs have a relatively high failure rate. Consequently, mesh or grafts have been used to provide additional support for a traditional repair. However, the typical placement of such augmentation of the levator muscle is through a transvaginal approach, with transvaginal dissection. Such transvaginal dissection can be more difficult for the surgeon and may lead to further failures. Recent studies show that traditional transvaginal approaches for repair of levator muscle laxity result in a greater incidence of dyspaerunia (painful intercourse) as compared to alternative methods. Studies have also shown that traditional mesh repairs of rectocele repair show unacceptably high levels of mesh erosion. These problems, along with problems of recurrence of the rectocele, are likely due in part to ballooning of the levator muscles. Consequently, there is a need for alternative methods and apparatus for augmentative support of repaired levator muscle in cases of pelvic organ prolapse. Thus, the present invention is directed to improving the mesh anchorage in levatorplasty surgery. Such improvement in anchorage should result in greater longevity of the repair, by substantially minimizing ballooning of the levator musculature typically caused by stress events, such as coughing and sneezing.

SUMMARY OF THE INVENTION

The present invention is an improved method of repair of rectocele via levatorplasty. The invention encompasses a multi-level, tension-free repair that prevents or substantially minimizes levator ballooning by anchoring or pinning the rectocele posteriorly. The method is also adaptable to other urological applications, and may be used as a standalone treatment of prolapse, or may be used as supportive treatment augmenting other repairs of pelvic organ prolapse.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
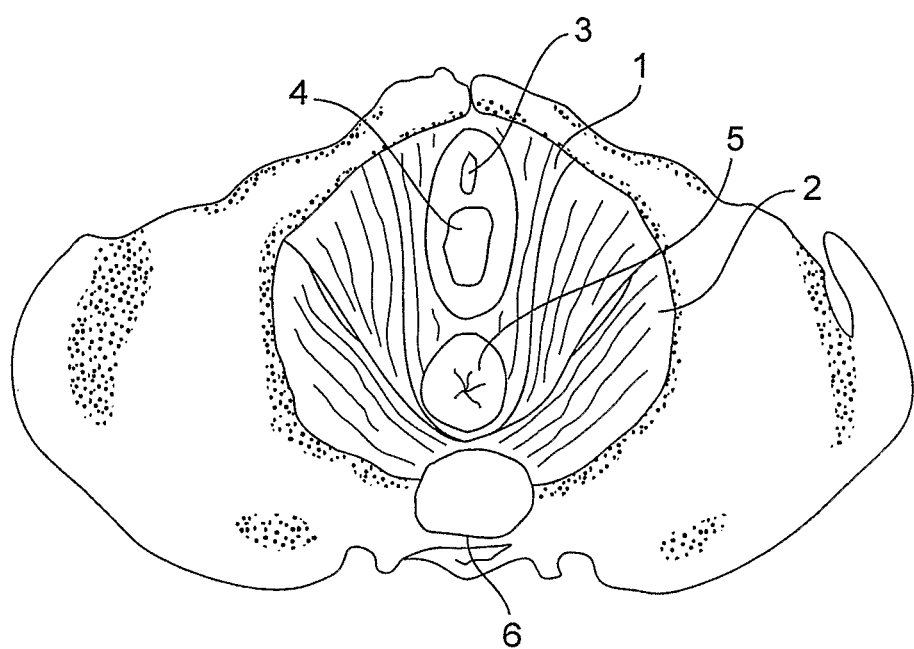
FIG. 1 shows the anatomy of the pelvic floor, including the pubococcygeus muscles and illiococcygeus muscles that make up the levator ani muscles.

Referring now to the drawings, wherein like reference numerals designate identical or corresponding parts throughout the several views. The following description is meant to be illustrative only, and not limiting other embodiments of this invention will be apparent to those of ordinary skill in the art in view of this description.

Figure 2:
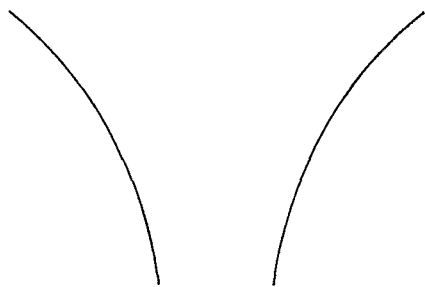
FIG. 2 shows a schematic illustrating the general condition of healthy levator muscles.
Figure 3:
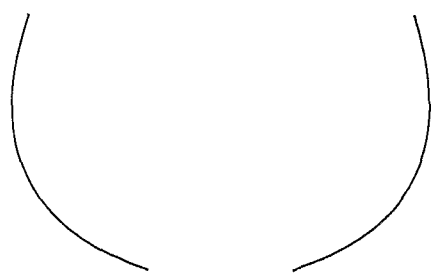
FIG. 3 shows a schematic illustrating the general condition of levator muscles associated with prolapsed pelvic organs.

The relevant female anatomy is illustrated in FIG. 1. As can be seen, the levator ani muscles, including the pubococcygeus muscles 1 and illiococcygeus muscles 2, are a significant portion of the pelvic floor and provide support for the pelvic viscera. Also illustrated in FIG. 1 are the urethra 3, vagina 4, rectum 5 and sacrum 6 of the female patient. FIGS. 1 and 2 show the normal condition of the levator muscles, while FIG. 3 shows the posture of levator muscles associated with prolapsed pelvic organs. As can be seen, such muscles offer less support for the pelvic viscera and may benefit from additional support as provided in the present invention. Further, laxity of such muscles is thought to result in an increased size of the normal opening in the muscles at the urogenital hiatus. With this increased size, there is a tendency of the organs in the anatomical vicinity to fill the opening. This would explain some degree of prolapse. However, this degree of prolapse caused by the organs filing the open space in the pelvic floor, can lead to increased stress on the normal fascia supports for these organs. This leads to failure of this connective tissue, resulting in further prolapse through the pelvic floor opening.

There are generally considered to be three anatomical levels of pelvic organ support. Level 1 is the cardinal/uterosacral ligament complex. Level 2 is the rectovaginal fascia. Level 3 is the perineal body. In the present invention, two levels of repair are used to repair a rectocele. Implants at both levels are used, and may be made from a suitable synthetic material, such as polypropylene. Alternatives may include use of biological materials, or a combination of biological materials and synthetic materials. The implant may be of any shape suitable for providing adequate support of the levator musculature.

Figure 4:
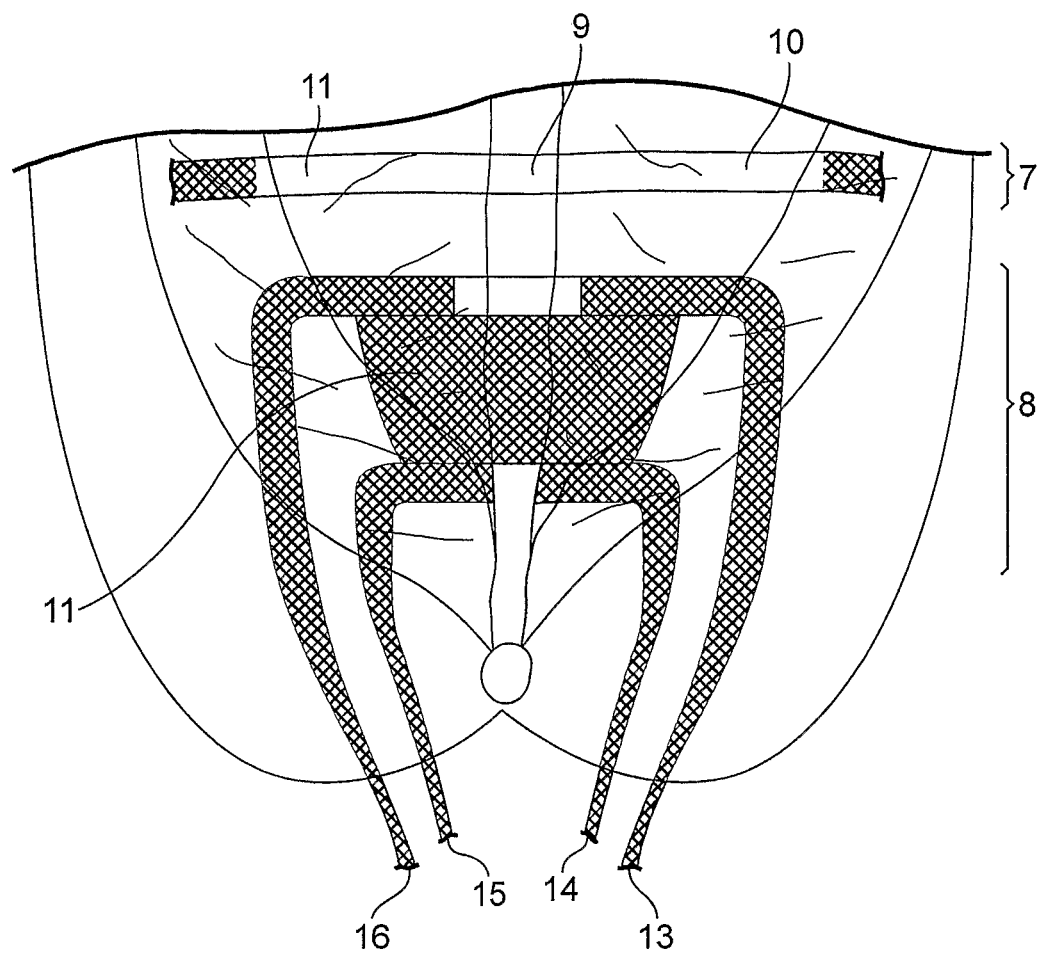
FIGS. 4 and 5 show an embodiment of the method of the present invention.
Figure 5:
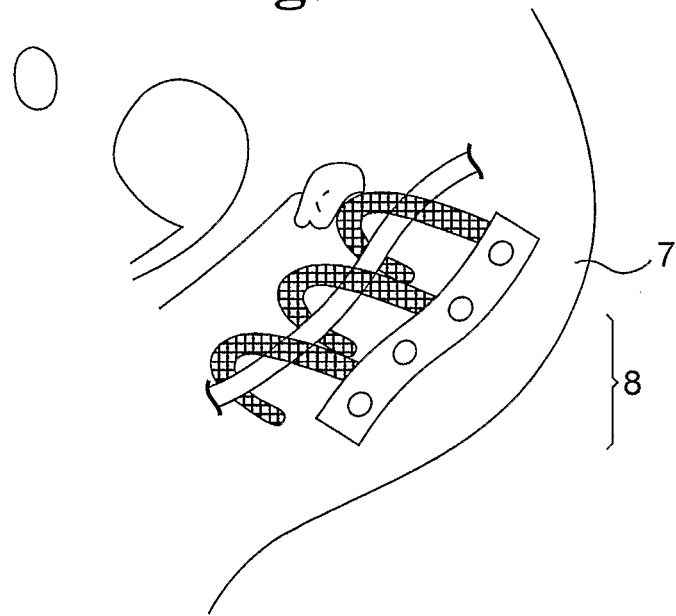

In a preferred embodiment, illustrated in FIGS. 4 and 5, a level 1 repair is performed, along with a level 2 repair. The level 1 repair comprises placement of a suitable implant in a position 7 to support the prolapsed organ in its normal position in an anterior location. The level 1 repair may comprise placement of a support member having a central support portion 9 and two end portions 10, 11 extending therefrom, as disclosed in U.S. Publication 2005/0245787, herein expressly incorporated by reference. Further, the placement of the implant in the level 1 repair may be effected by the methods disclosed in U.S. Publication 2005/0245787.

Figure 6:
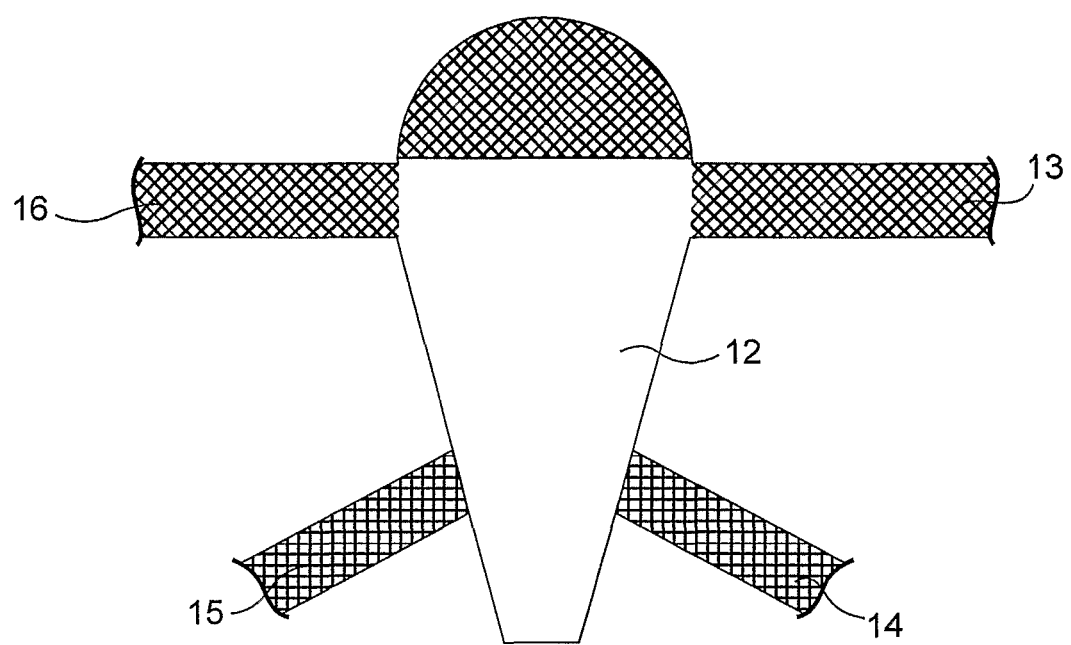
FIG. 6 shows the mesh implant of the present invention.

The preferred level 2 repair accompanies the level 1 repair. In the level 2 repair, a supportive implant is placed in a position 8 posterior to the level 1 repair. The implant used in the level 2 repair may comprise a support member having a central support portion 12 and four end portions 13, 14, 15, 16 extending therefrom, as disclosed in U.S. Publication 2005/0250977, herein expressly incorporated by reference, and the method for implanting said support member may be the method disclosed in U.S. Publication 2005/0250977, herein incorporated by reference. U.S. Pat. Nos. 6,802,807, 6,911,003, 7,048,682, and 6,971,986 are also incorporated by reference. See also FIG. 6.

The level 2 repair complements the level 1 repair, and is situated lower and posterior to the level 1 repair, as illustrated in FIG. 4. In one embodiment, the implant having four end portions 13, 14, 15, 16 is placed wherein the first and second end portions 14, 15 are placed in a lower and more posterior location, with the third and fourth end portions 13, 16 being placed in an anterior position relative to the first and second end portions 14, 15. The support portion 12 of said implant, to which said end portions 13, 14, 15, 16 are attached, is placed in a position to support said prolapsed organ.

The implant may be of any shape suitable for providing adequate support of the levator musculature. The implant of the present invention may be made of a synthetic or non-synthetic material, or a combination thereof. Suitable non-synthetic materials include allografts, homografts, heterografts, autologous tissues, cadaveric fascia, autodermal grafts, dermal collagen grafts, autofascial heterografts, whole skin grafts, porcine dermal collagen, lyophilized aortic homografts, preserved dural homografts, bovine pericardium and fascia lata. Commercial examples of synthetic materials include Marlex™ (polypropylene) available from Bard of Covington, R.I., Prolene™ (polypropylene), Prolene Soft Polypropylene Mesh or Gynemesh (nonabsorbable synthetic surgical mesh), both available from Ethicon, of New Jersey, and Mersilene (polyethylene terphthalate) Hernia Mesh also available from Ethicon, Gore-Tex.TM. (expanded polytetrafluoroethylene) available from W. L. Gore and Associates, Phoenix, Ariz., and the polypropylene sling available in the SPARC™ sling system, available from American Medical Systems, Inc. of Minnetonka, Minn., Dexon™ (polyglycolic acid) available from Davis and Geck of Danbury, Conn., and Vicryl™ available from Ethicon.

Other examples of suitable materials include those disclosed in published U.S. patent application Ser. No. 2002/0072694. More specific examples of synthetic materials include, but are not limited to, polypropylene, cellulose, polyvinyl, silicone, polytetrafluoroethylene, polygalactin, Silastic, carbon-fiber, polyethylene, nylon, polyester (e.g. Dacron) polyanhydrides, polycaprolactone, polyglycolic acid, poly-L-lactic acid, poly-D-L-lactic acid and polyphosphate esters. See Cervigni et al., The Use of Synthetics in the Treatment of Pelvic Organ Prolapse, Current Opinion in Urology (2001), 11: 429435.

In a preferred embodiment, a suitable delivery needle is attached to a first end portion of said implant. An initial incision is made on a first side of the rectum approximately 2 cm lateral and 2 cm posterior to the anus of the patient. The needle with attached implant is delivered to the appropriate anatomical position.

Obviously, numerous modifications and variations of the present invention are possible in light of the above teachings. It is therefore to be understood that within the scope of the appended claims, the invention may be practiced otherwise than as specifically described herein.

The invention claimed is:

1. A method for performing pelvic repair, the method comprising
   providing an implant useful to perform a level 1 repair of a cardinal/uterosacral ligament complex;
   providing an implant comprising a central support portion and four end portions extending therefrom, useful to perform a level 2 repair of rectovaginal fascia; and
   placing the implant useful to perform a level 1 repair at a location to support tissue of a cardinal/uterosacral ligament complex,
   placing the implant useful to perform a level 2 repair at a location to support rectovaginal fascia, so that third and fourth end portions of the four end portions are placed in an anterior position relative to first and second end portions of the four end portions, and
   passing a needle through an external skin incision, the needle attached to either the implant useful to perform a level 1 repair or the implant useful to perform a level 2 repair, wherein the incision is present on a first side of a rectum and posterior to an anus.

2. The method of claim 1 wherein the implant useful to perform a level 1 repair comprises a central support portion and two end portions extending therefrom.

3. The method of claim 1 wherein the implant useful to perform a level 2 repair is placed to have the central support portion in a position to support a prolapsed organ.

4. A method for performing pelvic repair, the method comprising
   providing an implant useful to perform a level 1 repair of a cardinal/uterosacral ligament complex;
   providing an implant comprising a central support portion and four end portions, the central support portion comprising first, second, third and fourth sides, with two of the four end portions extending from the first side and two of the four end portions extending from the third side, the implant useful to perform a level 2 repair of rectovaginal fascia; and
   placing the implant useful to perform a level 1 repair at a location to support tissue of a cardinal/uterosacral ligament complex,
   placing the implant useful to perform a level 2 repair at a location to support tissue of the rectovaginal fascia, and
   passing a needle through an external skin incision, the needle attached to either the implant useful to perform a level 1 repair or the implant useful to perform a level 2 repair, wherein the incision is present on a first side of a rectum and posterior to an anus.

5. The method of claim 4 wherein the implant useful to perform a level 1 repair comprises a central support portion and two end portions extending therefrom.

* * * * *

UNITED STATES PATENT AND TRADEMARK OFFICE
CERTIFICATE OF CORRECTION

PATENT NO.       : 8,585,577 B2
APPLICATION NO.  : 12/087552
DATED            : November 19, 2013
INVENTOR(S)      : Rane Page 1 of 1

It is certified that error appears in the above-identified patent and that said Letters Patent is hereby corrected as shown below:

In the Specification

In Column 1, Line 59, delete "fission" and insert -- fusion --, therefor.

In Column 3, Lines 43-44, delete "dyspaerunia" and insert -- dyspareunia --, therefor.

In Column 4, Line 12, delete "illiococcygeus" and insert -- iliococcygeus --, therefor; and Column 4, Line 33, delete "illiococcygeus" and insert -- iliococcygeus --, therefor.

In Column 5, Line 54, delete "polygalactin," and insert -- polyglactin, --, therefor; and Column 5, Line 60, delete "11: 429435." and insert -- 11: 429-435. --, therefor.

In the Claims

In Column 6, Lines 12-13, in Claim 1, delete "comprising" and insert -- comprising: --, therefor.

In Column 6, Lines 39-40, in Claim 4, delete "comprising" and insert -- comprising: --, therefor.

Signed and Sealed this
Second Day of June, 2015

Michelle K. Lee
*Director of the United States Patent and Trademark Office*

UNITED STATES PATENT AND TRADEMARK OFFICE
CERTIFICATE OF CORRECTION

PATENT NO. : 8,585,577 B2  
APPLICATION NO. : 12/087552  
DATED : November 19, 2013  
INVENTOR(S) : Ajay Rane Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1027 days.

Signed and Sealed this

Twenty-second Day of September, 2015

Michelle K. Lee
*Director of the United States Patent and Trademark Office*